United States Patent
Noll et al.

[11] Patent Number: 5,876,420
[45] Date of Patent: Mar. 2, 1999

[54] MEDICAL INSTRUMENT WITH RELESABLE LOCK

[75] Inventors: Thomas J. Noll, St. Louis Park; Daryl Kiefer, Fridley; Michael C. Chappuis, Bloomington; Robert C. Collins, Eden Prairie, all of Minn.

[73] Assignee: Innomedica, Bloomington, Minn.

[21] Appl. No.: 905,108

[22] Filed: Aug. 1, 1997

Related U.S. Application Data

[63] Continuation-in-part of Ser. No. 595,233, Feb. 1, 1996, Pat. No. 5,653,729.

[51] Int. Cl.⁶ .................................................. A61B 17/28
[52] U.S. Cl. ........................................... 606/208; 606/206
[58] Field of Search ..................................... 606/205–211

[56] References Cited

U.S. PATENT DOCUMENTS

| | | |
|---|---|---|
| 1,066,925 | 7/1913 | Lancaster . |
| 3,654,930 | 4/1972 | Hobbs, II . |
| 3,911,766 | 10/1975 | Fridolph . |
| 4,432,352 | 2/1984 | Wineland . |
| 4,435,352 | 3/1984 | Olsen . |
| 4,461,297 | 7/1984 | Sutter . |
| 4,462,404 | 7/1984 | Schwarz . |
| 4,598,561 | 7/1986 | Girard . |
| 4,646,755 | 3/1987 | Kane . |
| 4,685,314 | 8/1987 | Geenwalt . |
| 4,722,339 | 2/1988 | Dreier . |
| 4,823,792 | 4/1989 | Dulebohn . |
| 4,912,949 | 4/1990 | Bowers . |
| 4,917,677 | 4/1990 | McCarthy . |
| 4,972,847 | 11/1990 | Dutcher et al. . |
| 5,040,545 | 8/1991 | Dutcher et al. . |
| 5,143,090 | 9/1992 | Dutcher et al. . |
| 5,156,431 | 10/1992 | Lowe . |
| 5,196,023 | 3/1993 | Martin . |
| 5,217,028 | 6/1993 | Dutcher et al. . |
| 5,236,436 | 8/1993 | Koros et al. . |
| 5,250,072 | 10/1993 | Jain . |
| 5,255,693 | 10/1993 | Dutcher et al. . |
| 5,304,188 | 4/1994 | Marogil . |
| 5,336,228 | 8/1994 | Cholhan ................................. 606/208 |
| 5,368,596 | 11/1994 | Burkhart . |
| 5,464,413 | 11/1995 | Siska, Jr. et al. ....................... 606/208 |
| 5,704,925 | 1/1998 | Otten et al. ............................. 606/208 |

FOREIGN PATENT DOCUMENTS

| | | | |
|---|---|---|---|
| 0065432 | 7/1996 | Germany ................................. 606/208 |

*Primary Examiner*—Michael Buiz
*Assistant Examiner*—Kevin Truong
*Attorney, Agent, or Firm*—Palmatier, Sjoquist, Voigt & Christensen, P.A.

[57] ABSTRACT

An improved medical instrument with a releasable lock interposed between the handles of the medical instrument to hold the jaws in closed position to grip an object. The lock has at least one flexible finger and a plurality of movable sleeves that allow one hand operation to selectively lock and release the jaws without substantial lateral displacement of the object. A plurality of locking stops is provided so that the jaws may be held closed at a variety to tensions, to accommodate a variety of objects.

23 Claims, 3 Drawing Sheets

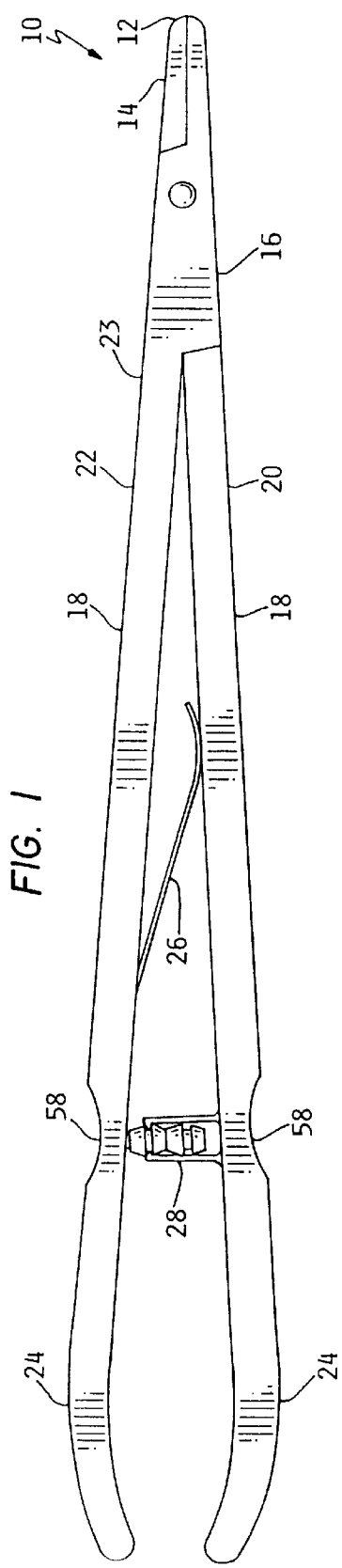
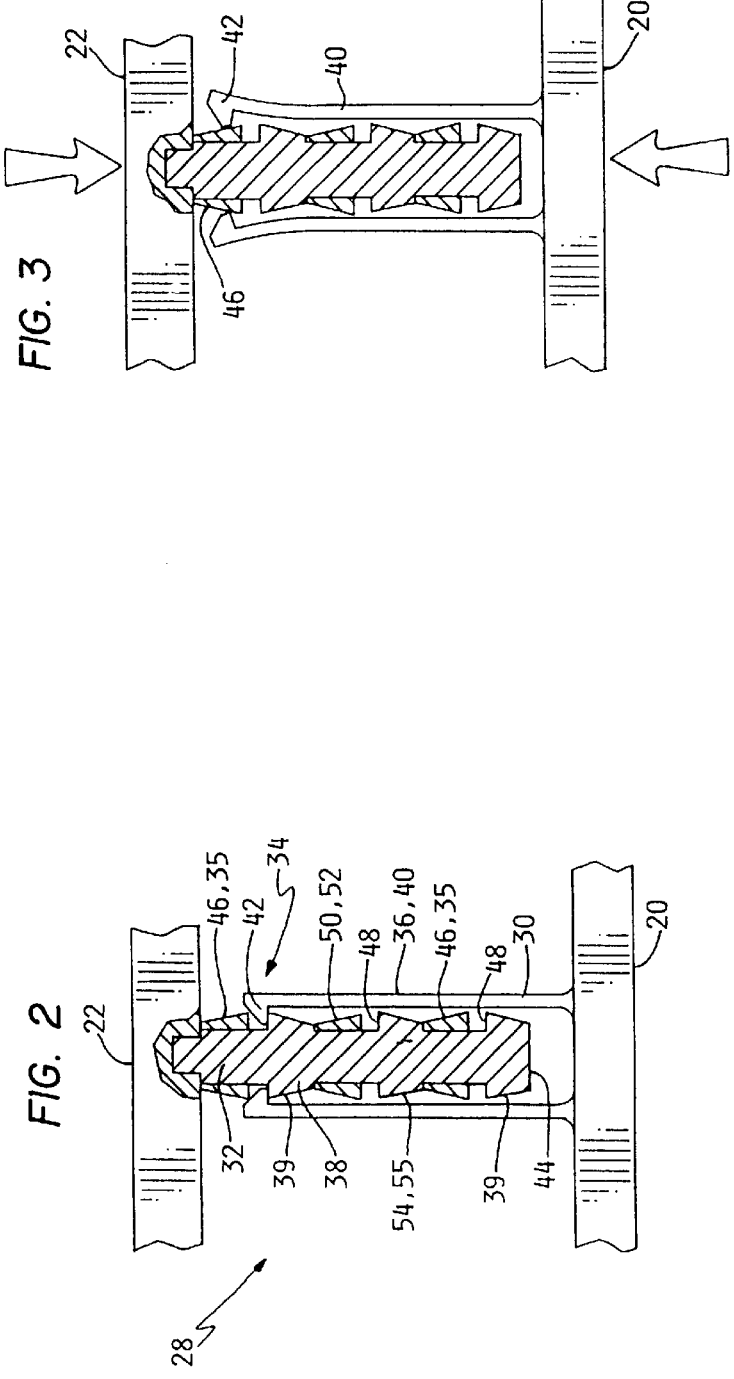

MEDICAL INSTRUMENT WITH RELESABLE LOCK

This application is a continuation-in-part application of U.S. Ser. No. 08/595,233; Filed Feb. 1, 1996 now U.S. Pat. No. 5,653,729 for Medical Instrument with Releasable Lock.

BACKGROUND OF THE INVENTION

The invention relates to medical instruments having a jaw or jaws for clamping, grasping, or holding medical devices and/or portions of an individual's anatomy.

Conventional medical instruments (needle holders, forceps, etc.) may be used by a physician to manipulate the handles to hold and work the grasping jaws for various medical procedures. Conventional forceps and needle holders are fabricated from a pair of rigid parts each having a jaw at one end and a handle with a ring at the other end. The two parts are mounted together to form a scissors-like instrument. The two parts are pivotally secured behind the pair of jaws. There is a finger ring and a thumb ring at the distal end of each handle. The physician places his thumb in one ring and his index finger in the other ring to control and manipulate the tool or instrument. He can squeeze the two rings together with his thumb and finger to cause the jaws to clamp down. The conventional forcep requires squeezing of the handle while simultaneously manipulating the forcep. Some instruments have engageable snap together locking means on the pair of handles and towards the rings to lock the jaws shut by locking the pair of handles together. It is usually a snap connection. The lock will engage when sufficient force is supplied by the finger and thumb to press the rings together. The lock will disengage when sufficient force is applied to spread apart the rings.

The disadvantage of this type of locking instrument is that substantial side force must be used to unlock the handles. Sometimes, this requires the use of two hands. If one hand is used to spread apart the rings, the forceps may suddenly move laterally as the rings disengage, potentially causing collateral damage or puncture of a delicate organ or blood vessel. Physicians often need the other hand for holding onto the skin or organ and cannot spare that hand to help to disengage the clamped instrument.

There is a need for medical instruments with an improved locking arrangement which allows the physician to lock and unlock the instrument using only one hand, and without imposing any side-to-side motion of the instrument as the jaws unlock.

Medical instruments come in various sizes and are used for particular medical procedures. Thus, a medical instrument must be capable of clamping onto a variety of objects including, but not limited to surgical needles, vessels, and/or organs. There is thus a need for a tension adjustment for the jaws of the medical instrument. The tension must be adjustable with only one hand.

SUMMARY OF THE INVENTION

An improved medical instrument with a releasable lock interposed between the handles of the instrument to hold the jaws in closed position to grip the desired object. The lock has at least one flexible finger and a plurality of movable sleeves that allow one hand operation to selectively lock and release the jaws without substantial lateral displacement. A plurality of locking stops is provided so that the jaws may be held closed at a variety of tensions, to accommodate a variety of objects.

A principal object of the invention is to provide an instrument which allows a physician to lock and unlock the instrument onto the object using only one hand, and without imposing any side-to-side motion of the instrument as the jaws unlock.

A second principal object of the invention is to provide a tension adjustment, operable by one hand, for clamping the instrument onto a variety of objects of various sizes.

A feature of the present invention includes a releasable locking device interposed between the handles permitting one-handed tension adjustment of the medical instrument.

Another feature of the present invention is a locking mechanism including at least one flexible finger and a plurality of movable sleeves permitting one-handed operation of the medical instrument.

Still another feature of the present invention is a plurality of locking stops adapted for engagement to the flexible finger or fingers permitting the locking of the jaws at a variety of tensions to accommodate a variety of objects.

BRIEF DESCRIPTION OF THE DRAWINGS

FIG. 1 is a plan view of a surgical needle holder which is one example of a medical instrument.

FIG. 2 is a detail of the locking mechanism partially broken away, showing the locking mechanism in the locked position at highest tension.

FIG. 3 is an alternate detail of the locking mechanism partially broken away, showing details of how the fingers are unlocked by pressing the handles toward one another.

DETAILED DESCRIPTION OF THE PREFERRED EMBODIMENTS

Figure 4:
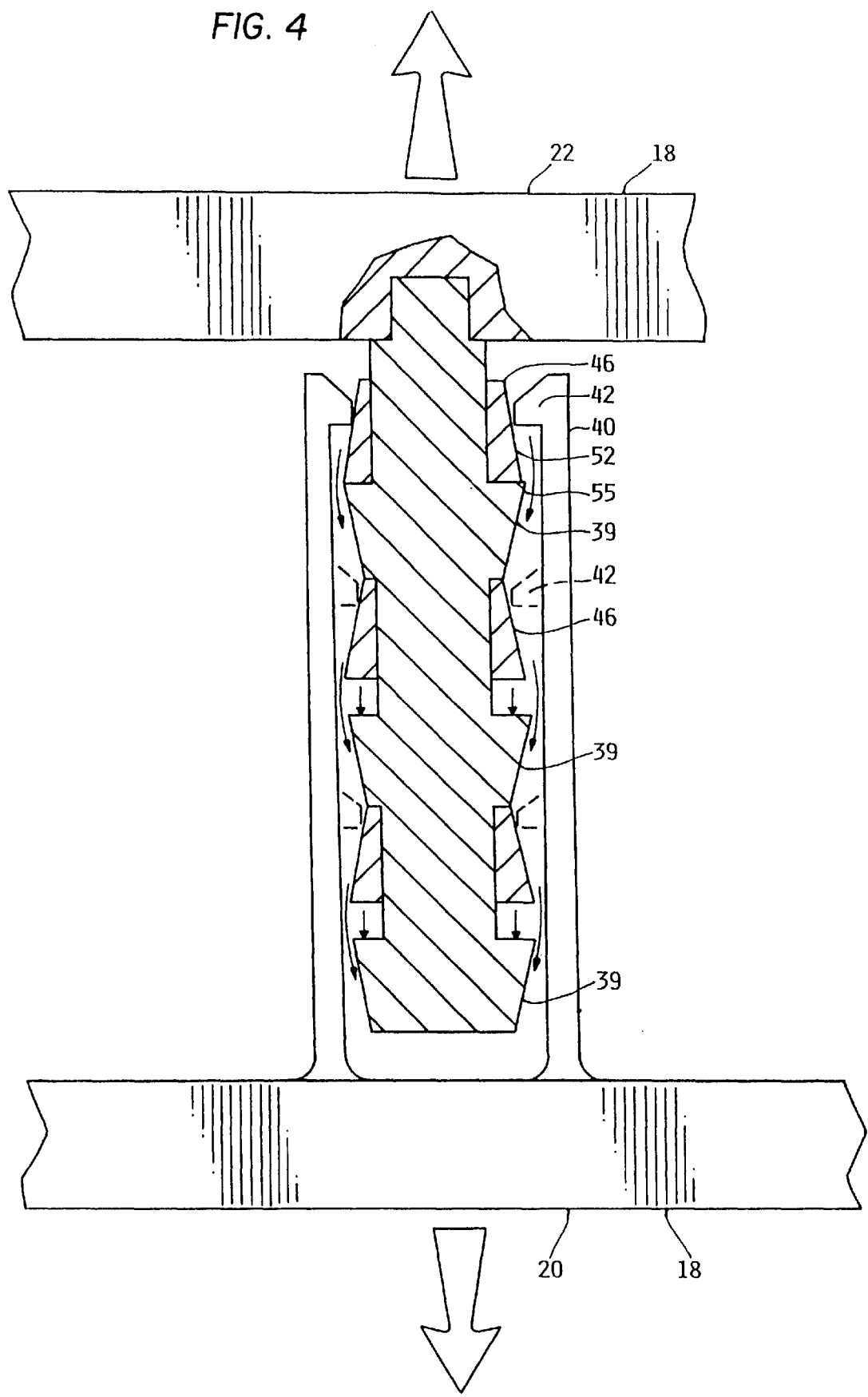
FIG. 4 is an alternate detail of the locking mechanism partially broken away, showing details of how the fingers and sleeves cooperate to completely unlock the medical instrument.

FIG. 1 shows a medical instrument 10 employing the present invention. FIG. 1 shows an example of a needle holder without finger and thumb rings. The needle holder 10 comprises a pair of pivotally-connected scissor jaws 12. The jaws 12 have jaw ends 14 for grasping a surgical needle and thread, and attachment ends 16.

A pair of spaced apart angularly opposed handle bodies 18, comprising a first handle 20 and a second handle 22, have first ends 23 and second ends 24. The first ends 23 may be secured in tandem with the attachment ends 16 of the jaws 12, thereby operating the jaws.

A spring 26 may be located approximately midway between the first ends 23 and the second ends 24. The spring 26 is preferably attached to one of the handle bodies 18 and biases against the other handle body 18. The spring 26 preferably functions to keep the handle bodies 18 spread apart and the jaws 12 open when at the at-rest position.

The medical instrument 10 may also include a releasable lock means 28 mounted between the handle bodies 18. As will be seen, a physician may operate the lock means 28 with one hand, either to lock a needle into the medical instrument 10 or to release the lock means 28 to remove a needle from the medical instrument 10. The releasable lock means 28 described herein may also function to selectively connect and release any two members at a series of spaced positions relative to each other.

The releasable lock means 28 further comprises a first means 30 secured to the first handle 20 and a second means 32 secured to the second handle 22. A releasable cooperating means 34 preferably holds the first handle 20 and second handle 22 adjacent each other, thereby retaining the jaws 12 in the closed position. The releasable cooperating means 34 also operates to release the first means 30 and second means 32, thus allowing the first handle 20 and second handle 22 to move away from each other and the jaws 12 to move to the open position.

In one embodiment, the first means 30 includes finger means 36 secured to the first handle 20. The second means 32 includes holding means 38 engageable with the finger means 36 to hold the first handle 20 and second handle 22 adjacent each other. The cooperating means 34 includes sliding means 35 to release the finger means 36 from the holding means 38, allowing the first handle 20 and second handle 22 to move away from each other and the jaws 12 to move to the open position.

In another embodiment, the finger means 36 comprises a pair of flexible fingers 40 having hooks 42. The holding means 38 may include a head 39 engageable with the hooks 42 to hold the first handle 20 and second handle 22 adjacent each other. The releasable cooperating means 34 operates to release the hooks 42 from the head 39 when the first handle 20 and second handle 22 are moved toward each other.

In another embodiment, the holding means 38 comprises a plurality of heads 39 and a plurality of releasable cooperating means 34. This arrangement forms a tension adjustment which allows the first handle 20 and second handle 22 to be moved towards each other in a series of steps thereby locking the jaws 12 closer and closer together. With this tension adjustment, the medical instrument 10 may be used to tightly hold needles with varying thicknesses without bending or damaging the needles or items. The releasable cooperating means 34 operates to release the hooks 42 from all heads 39 when the first handle 20 and second handle 22 are moved toward each other.

The heads 39 may be mounted on a projection 44 secured to the second handle 22. Surrounding the projection 44 may be movable sleeve means 46 which are the sliding means 35 to release the finger means 36. The hooks 42 engage a shoulder 48 on the head 39 to hold the first handle 20 and second handle 22 adjacent each other. The sleeve means 46 may be spaced from the shoulder 48 to allow the hooks 42 to engage the shoulder 48.

The sleeve means 46 may be frustoconical in cross-section, as shown in FIG. 2. The sleeve means 46 may be oriented on the projection 44 such that the outer walls 50 of the sleeve means 46 converge toward each other in the direction away from the fingers 40. In this manner, the outer walls 50 form a wedge 52.

In like manner, the head 39 may also be frustoconical in cross-section and may be oriented on the projection 44 such that the outer walls 54 of the head 39 converge toward each other in the direction toward the fingers 40, thus forming a wedge 55.

As will be described below, the wedge 52 and the wedge 55 meet during disengagement of the fingers 40 to form a smooth surface over which the hooks 42 may pass.

To lock a needle into the medical instrument 10, the physician places the open jaws 12 around the needle and squeezes the handles 18 together. As the handles 18 move toward each other, the hooks 42 slide along the wedge 55 of the head 39 closest to the first handle 20. The hooks 42 then engage the first shoulder 48.

If additional closing pressure or tension is required to hold the needle firmly in the holder 10, the physician continues to squeeze the handles 18 together, causing the hooks 42 to disengage from the shoulder 48 and pass over the wedge 52 of the first sleeve 46, and over the wedge 55 of the next head 39 until the next shoulder 48 is reached. This process continues until the desired tension is reached. The physician then releases pressure from the handles 18, and the hooks 42 are held against the shoulder 48 by the spring 26.

To release the needle or item from the medical instrument 10, the physician squeezes the handles 18 toward each other, most preferentially at the indentations 58. Enough pressure is exerted so that the fingers 40 move onto the sleeve means 46 nearest their point of engagement as seen in FIG. 3. Because the fingers 40 are flexible, they deflect outwardly as they move onto the sleeve means 46.

The physician then releases pressure on the handles 18. The fingers 40, having moved onto the sleeve means 46, now grasp this movable sleeve 46 as the handles 18 move away from each other under spring force due to the spring 26 or jaw end 14 tension. As seen in FIGS. 3 and 4, the hooks pull the sleeve 46 toward the head 39 until the sleeve 46 abuts the next head 39, at which point the wedge 52 forms a smooth surface with or is slightly higher than the wedge 55. As the handles continue to move away from each other, the fingers 40, as shown by the arrows, move over the surface, past the head 39, and onto the next sleeve 46. The hooks 42 (shown in phantom) grasp the next sleeve 46, pull the sleeve 46 toward the next head 39 until the sleeve 46 abuts the head 39, and the fingers move over the smooth surface formed by this junction. The above process continues until the hooks 42 have disengaged from all heads 39. Then the handles 18 may be moved completely away from each other, releasing the needle.

Figure 5:
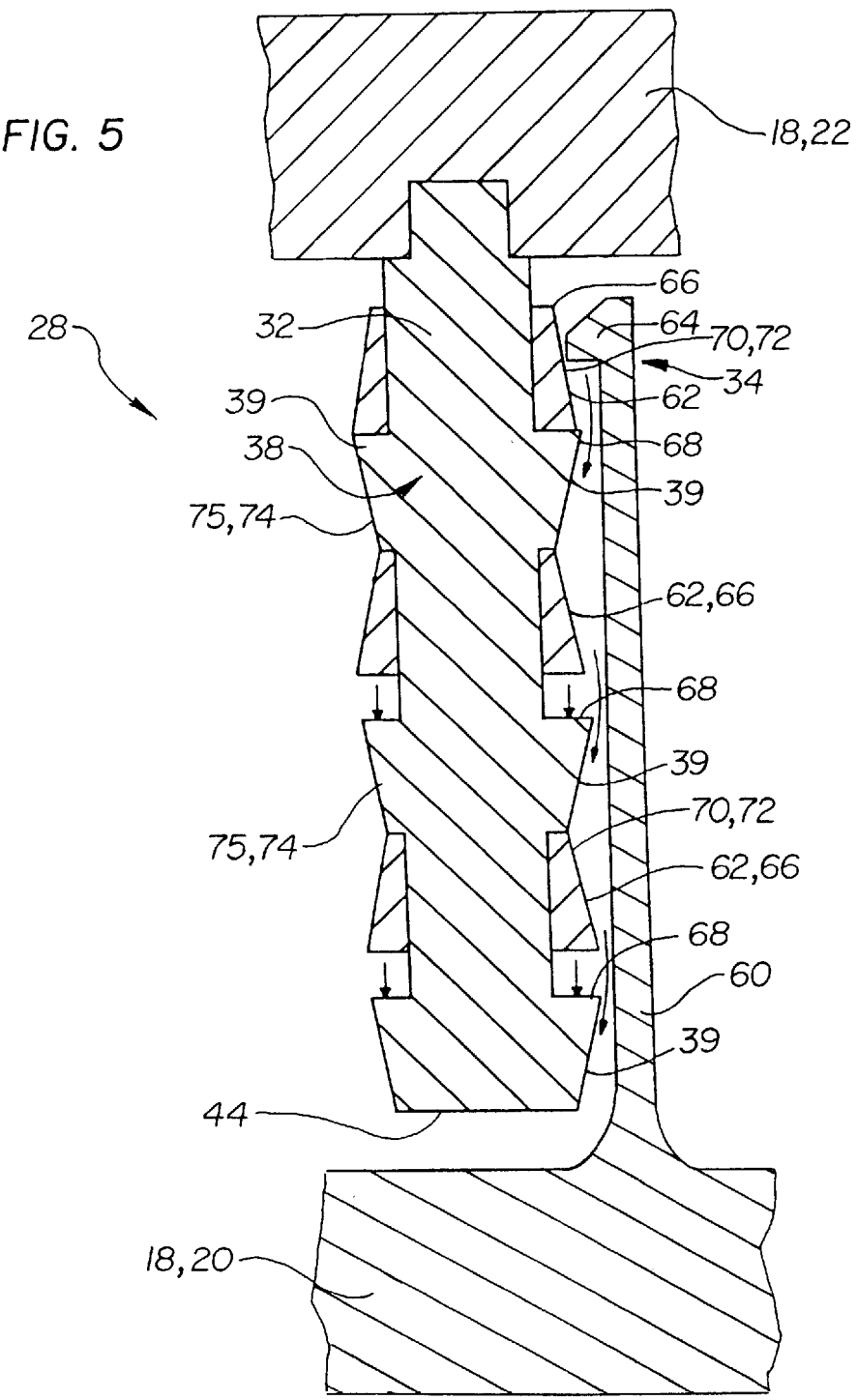
FIG. 5 is an alternate detail of the locking mechanism partially broken away, showing details of how a single finger and plurality of sleeves cooperate to completely unlock the medical instrument.

The medical instrument 10 may also include an alternative releasable lock means 28 mounted between the handle bodies 18 as depicted in FIG. 5. A physician may operate the alternative lock means 28 with one hand, either to lock a needle or other item into the medical instrument 10 or to release the alternative lock means 28 to remove a needle or item from the medical instrument 10. The alternative releasable lock means 28 described herein may also function to selectively connect and release any two members at a series of spaced positions relative to each other.

The alternative releasable lock means 28 includes a single finger means 60 secured to the first handle 20. In this embodiment, the second means 32 includes holding means 38 engageable with a single finger means 60 to hold the first handle 20 and second handle 22 adjacent to each other. In this embodiment, the cooperating means 34 includes sliding means 62 which function to release the single finger means 60 from the holding means 38, allowing the first hand 20 and the second hand 22 to move away from each other and the jaws 12 to move to the open position.

In this embodiment, the single finger means 60 comprises a hook 64. The holding means 38 may include a head 39 engageable with the hook 64 to hold the first handle 20 and second handle 22 adjacent to each other. The releasable cooperating means 34 operates to release the hook 64 from the head 39 when the first handle 20 and second handle 22 are moved toward each other.

In this embodiment, the holding means 38 may comprise a plurality of heads 39 and a plurality of releasable cooperating means 34. This arrangement forms a tension adjustment which allows the first handle 20 and the second handle 22 to be moved toward each other in a series of steps, thereby locking the jaws 12 closer and closer together. With this tension adjustment, the medical instrument 10 may be used to tightly hold needles or other objects with varying thicknesses without bending the needles or damaging the other objects. The releasable cooperating means 34 operates to release the hook 64 from all heads 39 when the first handle 20 and second handle 22 are moved toward each other.

The heads 39 may be mounted on a projection 44 secured to the second handle 22. Surrounding the projection 44 may be moveable sleeve means 66 which are the sliding means 62 to release the single finger means 60. The hook 64 engages a shoulder 68 on the head 39 to hold the first handle 20 and the second handle 22 adjacent to each other. The moveable sleeve means 66 may be spaced from the shoulders 68 to allow the hook 64 to engage the shoulder 68.

The moveable sleeve means 66 may be frustoconical in cross-section, as shown in FIG. 5. The moveable sleeve means 66 may be oriented on the projection 44 such that the outer walls 70 of the moveable sleeve means 66 converge toward each other in the direction away from the single finger means 60. In this manner, the outer walls 70 form a wedge 72.

In like manner, the head 39 may also be frustoconical in cross-section and may be orientated on the projection 44 such that the outer walls 74 of the head 39 converge toward each other in the direction toward the single finger means 60 thus forming a wedge 75.

The wedge 72 and the wedge 75 meet during disengagement of the single finger means 60 to form a smooth surface over which the hook 64 may pass.

To lock a needle into the medical instrument 10, the physician places the open jaws 12 around the needle and squeezes the handles 18 together. As the handles 18 move toward each other, the hook 64 slides along the wedge 75 of the head 39 closest to the first handle 20. The hook 64 then engages the first shoulder 68.

If additional closing pressure or tension is required to hold the needle firmly in the medical instrument 10, the physician continues to squeeze the handles 18 together, causing the hook 64 to disengage from the first shoulder 68 to pass over the wedge 72 of the first sleeve 66, and over the wedge 75 of the next head 39 until the next shoulder 68 is reached.

This process continues until the desired tension is reached. The physician then releases pressure from the handles 18, and the hook 64 is held against the shoulder 68 by the spring 26.

To release the needle from the holder 10, the physician squeezes the handles 18 toward each other, most preferably at the indentations 58. Enough pressure is exerted so that the single finger means 60 move onto the sleeve means 66 nearest their point of engagement as seen in FIG. 5. Because the single finger means 60 is flexible, it may deflect outwardly as it moves onto the sleeve means 66.

The physician then releases pressure on the handles 18. The single finger means 60, having moved onto the sleeve means 66, now grasps this moveable sleeve 66 as the handles 18 move away from each other under spring force due to the spring 26 or jaw end 14 tension. As seen in FIG. 5, the hook 64 pulls the sleeve 66 toward the head 39 until the sleeve 66 abuts the next head 39, at which point the wedge 72 forms a smooth surface with, or is slightly higher than, the wedge 75. As the handles continue to move away from each other, the single finger means 60, as shown by the arrows, move over the surface, past the head 39 and onto the next sleeve 66. The hook 64 grasps the next sleeve 66, pulling the sleeve 66 toward the next head 39 until the sleeve 66 abuts the head 39, and the single finger means 60 moves over the smoother surface formed by this junction. The above process continues until the hook 64 has disengaged from all the heads 39. The handles 18 may be moved completely away from each other, releasing the needle.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. I claim a medical instrument for one-handed operation, comprising:
   (a) a pair of pivotally-connected scissor jaws having jaw ends and attachment ends, said jaw ends being used for grasping an object;
   (b) a pair of spaced apart angularly opposed handles, comprising a first handle and a second handle, each handle having first ends and second ends, said first ends being secured to and in tandem with said attachment ends of said pair of scissor jaws; and
   (c) a releasable lock means mounted between said handles operable by one hand to lock and unlock said scissor jaws against said object by manipulating said handles toward each other without substantial lateral motion of said instrument, said releasable lock means comprising a single finger secured to the first handle, a means for holding secured to the second handle, and a cooperating means for releasably engaging the single finger and the means for holding, permitting the first and second handles to move toward and away from each other in a series of steps to provide a tension adjustment between the first and second handles.

2. I claim the medical instrument of claim 1 further comprising a spring biased against said handles for keeping said jaws open and said handles spread apart when at the at-rest position.

3. I claim the medical instrument of claim 1, wherein said cooperating means assist in holding the first and second handles adjacent each other when the scissor jaws are retained in the closed position and assist in the release of the single finger from the means for holding when a first and second handles are moved away from each other and the scissor jaws move to the open position.

4. I claim the medical instrument of claim 3, wherein the means for holding engage the single finger to hold the first and second handles adjacent each other, said cooperating means comprising sliding means to release the single finger from the means for holding allowing the first and second handles to move away from each other.

5. I claim the medical instrument of claim 4, said single finger further comprising a hook, said means for holding comprising a head engageable with the hook to hold the first and second handles adjacent each other, said cooperating means being operable to release the hook from the head when the first and second handles are moved toward each other.

6. I claim the medical instrument of claim 5, said means for holding comprising a plurality of said heads and a plurality of said cooperating means, thereby forming a tension adjustment which allows the first and second handles to be moved toward each other in a series of steps and said cooperating means being operable to release the hook from all heads when the first and second handles are moved toward each other.

7. I claim the medical instrument of claim 1, said releasable lock means further comprising a projection secured to the second handle, a head mounted on said projection, said single finger engageable with said head to hold the first and second handles adjacent each other, and sleeve means surrounding said projection adapted to be engaged by said single finger to release the single finger from said head on movement of the single finger onto said sleeve means whereby the first and second handles move away from each other to release said scissor jaws.

8. I claim the medical instrument of claim 7, said single finger comprising a hook, said head having a shoulder engageable with the hook to hold the first and second handles adjacent to each other, said sleeve means being spaced from said shoulder to allow the hook to engage the shoulder, said hook being moveable onto the sleeve means to disengage the hook from the shoulder to allow the first and second handles to move away from each other.

9. I claim the medical instrument of claim 8, said sleeve means being frustoconical in cross-section having outer walls converging toward each other in the direction away from the single finger and forming a wedge over which said hook rides to disengage said hook from said shoulder, said head being frustoconical in cross-section, having first walls of said head converging in the direction toward the single finger and forming a wedge over which said hook rides to complete disengagement of the hook from said shoulder.

10. I claim the medical instrument of claim 9, further comprising a plurality of hook-engaging heads adjusted for releasable engagement to said sleeve means thereby forming a tension adjustment which allows the first and second handles to be moved toward each other in a series of steps and said sleeve means being operable to release the hook from all heads when the first and second handles are moved toward each other.

11. I claim a medical instrument for one-handed operation, comprising:
  (a) a pair of pivotally-connected scissor jaws having jaw ends and attachment ends, said jaw ends being used for grasping an object;
  (b) a pair of spaced apart angularly opposed handles, comprising a first handle and a second handle, each handle having first ends and second ends, said first ends being secured to and in tandem with said attachment ends of said pair of scissor jaws;
  (c) a spring, biased against said handles, for keeping said jaws open and said handles spread apart when at the at-rest position; and
  (d) a releasable lock means mounted between said handles operable by one hand to lock and unlock said scissor jaws against said object by squeezing said handles toward each other without substantial lateral motion of said instrument, said releasable lock means comprising a single finger secured to the first handle, a means for holding secured to the second handle, and a cooperating means for releasably engaging the single finger and the means for holding, permitting the first and second handles to move toward and away from each other in a series of steps to provide a tension adjustment between the first and second handles.

12. I claim the medical instrument of claim 11, wherein said cooperating means assist in holding the first and second handles adjacent each other when the scissor jaws are retained in the closed position and assist in the release of the single finger from the means for holding when the first and second handles are moved away from each other and the scissor jaws move to the open position.

13. I claim the medical instrument of claim 12, wherein the means for holding engage the single finger to hold the first and second handles adjacent each other, said cooperating means comprising sliding means to release the single finger from the means for holding, allowing the first and second handles to move away from each other.

14. I claim the medical instrument of claim 13, said single finger further comprising a hook, said means for holding comprising a head engageable with the hook to hold the first and second handles adjacent each other, said cooperating means being operable to release the hook from the head when the first and second handles are moved toward each other.

15. I claim the medical instrument of claim 14, said means for holding comprising a plurality of said heads and a plurality of said cooperating means, thereby forming a tension adjustment which allows the first and second handles to be moved toward each other in a series of steps and said cooperating means being operable to release the hook from all heads when the first and second handles are moved toward each other.

16. I claim the medical instrument of claim 11, said releasable lock means further comprising a projection secured to the second handle, a head mounted on said projection, said single finger engageable with said head to hold the first and second handles adjacent each other, and sleeve means surrounding said projection adapted to be engaged by said single finger to release the single finger from said head on movement of the single finger onto said sleeve means whereby the first and second handles move away from each other to release said scissor jaws.

17. I claim the medical instrument of claim 16, said single finger comprising a hook, said head having a shoulder engageable with the hook to hold the first and second handles adjacent each other, said sleeve means being spaced from said shoulder to allow the hook to engage the shoulder, said hook being movable onto the sleeve means to disengage the hook from the shoulder to allow the first and second handles to move away from each other.

18. I claim the medical instrument of claim 17, said sleeve means being frustoconical in cross-section having outer walls converging in the direction away from the single finger and forming a wedge over which said hook rides to disengage said hook from said shoulder, and said head is frustoconical in cross-section, having first walls of said head converging in the direction toward the single finger and forming a wedge over which said hook rides to complete disengagement of the hook from said shoulder.

19. I claim the medical instrument of claim 18, further comprising a plurality of hook-engaging heads adjusted for releasable engagement to said sleeve means thereby forming a tension adjustment which allows the first and second handles to be moved toward each other in a series of steps and said sleeve means being operable to release the hook from all heads when the first and second handles are moved toward each other.

20. I claim a medical instrument for one-handed operation, comprising:
  (a) a pair of pivotally connected scissor jaws having jaw ends and attachment ends, the jaw ends being used for grasping an object;
  (b) a pair of spaced apart angularly opposed handles, comprising a first handle and a second handle, each handle having first ends and second ends, said first ends being secured to, and in tandem with, said attachment ends of said pair of scissor jaws; and (c) a releasably lock means mounted between said handles operable by one hand to lock and unlock said scissor jaws against said object by manipulating said handles toward each other without substantial lateral motion of said instrument, said releasable lock means comprising a single finger secured to said first handle, said single finger comprising a hook, a projection secured to the second handle, a head mounted on said projection, said head having a shoulder engageable with the hook to hold the first and second handles adjacent to each other, said head being frustoconical in cross-section, having first walls of said head converging in the direction toward the single finger and forming a wedge over which said hook rides to complete disengagement of the hook from the shoulder, and sleeve means being frustoconical in cross-section having outer walls converging in the direction away from said single finger and forming a wedge over which said hook rides to disengage said hook from said shoulder, said sleeve means surrounding said projection and being spaced from said shoulder to allow said hook to engage said shoulder, said sleeve means being adapted to be engaged by said single finger to release the single finger from said head and the hook from the shoulders on movement of said finger onto said sleeve means whereby the first and second handles move away from each other to release said scissor jaws.

21. I claim the medical instrument of claim 20, further comprising a plurality of hook-engaging heads adjusted for releasable engagement to said sleeve means, thereby forming a tension adjustment which allows the first and second handles to be moved toward each other in a series of steps and said sleeve means being operable to release the hook from all heads when the first and second handles are moved toward each other.

22. I claim a medical instrument for one-handed operation, comprising:

(a) a pair of pivotally-connected scissor jaws having jaw ends and attachment ends, said jaw ends being used for grasping an object;

(b) a pair of spaced apart angularly posed handles, comprising a first handle and a second handle, each handle having first ends and second ends, said first ends being secured to, and in tandem with, said attachment ends of said pair of scissor jaws;

(c) a spring, biased against said handles, for keeping said jaws open and said handles spread apart when, at the at-rest position; and (d) a releasable lock means mounted between said handles operable by one hand to lock and unlock said scissor jaws against said object by squeezing said handles toward each other without substantial lateral motion of said instrument, said releasable lock means comprising a single finger secured to said first handle, said single finger comprising a hook, a projection secured to the second handle, a head mounted on said projection, said head having a shoulder engageable with the hook to hold the first and second handles adjacent to each other, said head being frustoconical in cross-section having first walls of said head converging in the direction toward the single finger and forming a wedge over which said hook rides to complete disengagement of the hook from said shoulder, and sleeve means being frustoconicai in cross-section having outer walls converging in the direction away from the single finger and forming a wedge over which the hook rides to disengage said hook from said shoulder, said sleeve means surrounding projection and spaced from said shoulder to allow said hook to engage said shoulder, said sleeve means being adapted to be engaged by said single finger to release the single finger from said head and the hook from the shoulder on movement of the single finger onto said sleeve means whereby the first and second handles move away from each other to release said scissor jaws.

23. I claim the medical instrument of claim 22, further comprising a plurality of hook-engaging heads adjusted for releasable engagement to said sleeve means, thereby forming a tension adjustment which allows the first and second handles to be moved toward each other in a series of steps and said sleeve means being operable to release the hook from all heads when the first and second handles are moved toward each other.

* * * * *